US010201671B2

(12) United States Patent
Levy

(10) Patent No.: US 10,201,671 B2
(45) Date of Patent: *Feb. 12, 2019

(54) PORTABLE MEDICAL GAS DELIVERY SYSTEM

(71) Applicant: Frank Levy, Fort Myers, FL (US)

(72) Inventor: Frank Levy, Fort Myers, FL (US)

(*) Notice: Subject to any disclaimer, the term of this patent is extended or adjusted under 35 U.S.C. 154(b) by 111 days.

This patent is subject to a terminal disclaimer.

(21) Appl. No.: 15/285,941

(22) Filed: Oct. 5, 2016

(65) Prior Publication Data
US 2017/0021115 A1 Jan. 26, 2017

Related U.S. Application Data

(63) Continuation of application No. 13/857,448, filed on Apr. 5, 2013, now Pat. No. 9,486,594, which is a
(Continued)

(51) Int. Cl.
A61M 13/00 (2006.01)
A61M 16/12 (2006.01)
(Continued)

(52) U.S. Cl.
CPC ...... A61M 13/003 (2013.01); A61M 16/0057 (2013.01); A61M 16/12 (2013.01); A61M 25/00 (2013.01); A61M 25/1018 (2013.01); A61M 25/10183 (2013.11); A61M 25/10185 (2013.11); A61M 39/221 (2013.01); A61M 2025/102 (2013.01); A61M 2202/0225 (2013.01); A61M 2205/3331 (2013.01)

(58) Field of Classification Search
CPC ............ A61M 13/003; A61M 25/1083; A61M 25/1085; A61M 16/12; A61M 39/221; A61M 25/10185; A61M 39/2211
See application file for complete search history.

(56) References Cited

U.S. PATENT DOCUMENTS 2,475,511 A 7/1949 Nicholson
2,828,889 A 4/1958 Joschko
(Continued)

FOREIGN PATENT DOCUMENTS

CN 2179152 Y 10/1994
DE 10161027 A1 6/2003
(Continued)

Primary Examiner — Edelmira Bosques
(74) Attorney, Agent, or Firm — Welsh Flaxman & Gitler LLC

(57) ABSTRACT

An apparatus for producing gas for use in medical applications. The apparatus includes a compressed gas unit having at least one container of compressed gas and a solenoid valve. An adjustable pressure regulator communicably connected to the gas container, separate and distinct from the solenoid valve, is adjusted to control the pressure of the gas provided from the container to the solenoid valve. An electrical power source is connected to the solenoid valve. A pressure activated electronic switch connected to the power source is responsive to a selected amount of voluntary fingertip pressure for opening the solenoid valve to transmit the gas therethrough to a conduit, which further transmits the gas to a destination for use or storage.

4 Claims, 3 Drawing Sheets

Related U.S. Application Data continuation-in-part of application No. 13/068,680, filed on May 17, 2011, now Pat. No. 8,876,749, which is a continuation-in-part of application No. 12/652,845, filed on Jan. 6, 2010, which is a continuation-in-part of application No. 12/210,368, filed on Sep. 15, 2008, which is a continuation-in-part of application No. 11/945,674, filed on Nov. 27, 2007, now Pat. No. 7,543,760.

(60) Provisional application No. 60/867,323, filed on Nov. 27, 2006.

(51) Int. Cl.
*A61M 16/00* (2006.01)
*A61M 25/10* (2013.01)
*A61M 25/00* (2006.01)
*A61M 39/22* (2006.01)

(56) References Cited

U.S. PATENT DOCUMENTS

| | | |
|---|---|---|
| 3,004,686 A | 10/1961 | McKee |
| 3,034,332 A | 5/1962 | Lederer |
| 3,831,844 A | 8/1974 | Tropeano et al. |
| 3,879,703 A | 4/1975 | Bonazoli et al. |
| 4,744,356 A | 5/1988 | Greenwood |
| 4,786,394 A | 11/1988 | Enzer et al. |
| 4,864,845 A * | 9/1989 | Chandler ........... G01N 15/0826 702/12 |
| 5,154,348 A | 10/1992 | Ratnik et al. |
| 5,395,318 A | 3/1995 | Kaprelian |
| 5,699,961 A | 12/1997 | Ratnik et al. |
| 6,125,846 A * | 10/2000 | Bathe .................... A61M 16/10 128/202.22 |
| 6,164,556 A | 12/2000 | Dupre et al. |
| 6,192,883 B1 | 2/2001 | Miller, Jr. |
| 6,295,007 B1 | 9/2001 | O'Meara |
| 6,402,047 B1 | 6/2002 | Thomas |
| 6,572,873 B1 | 6/2003 | Osman et al. |
| 6,895,952 B1 | 5/2005 | Bachelder |
| 6,997,347 B2 | 2/2006 | Peng et al. |
| 7,131,598 B2 | 11/2006 | Ratnik |
| 7,476,213 B2 | 1/2009 | Uesugi et al. |
| 7,543,760 B2 | 6/2009 | Levy et al. |
| 7,549,973 B2 | 6/2009 | Van Der Linden et al. |
| 7,552,731 B2 | 6/2009 | Jorczak et al. |
| 7,963,938 B2 | 6/2011 | Wollmann et al. |
| 9,744,342 B2 * | 8/2017 | Levy .................... A61M 35/003 |
| 2002/0174578 A1 | 11/2002 | Ross |
| 2006/0074386 A1 | 4/2006 | Wollmann |
| 2011/0152850 A1 | 6/2011 | Niedbala et al. |

FOREIGN PATENT DOCUMENTS

| | | |
|---|---|---|
| EP | 2468204 A1 | 6/2012 |
| WO | WO00/72821 | 12/2000 |
| WO | WO02/41872 | 5/2002 |
| WO | WO2005/048984 | 6/2005 |

\* cited by examiner

PORTABLE MEDICAL GAS DELIVERY SYSTEM

RELATED APPLICATIONS

This application is a continuation of U.S. patent application Ser. No. 13/857,448 filed Apr. 5, 2013, which is currently pending, which is a continuation in part of U.S. patent application Ser. No. 13/068,680 filed May 17, 2011, now U.S. Pat. No. 8,876,749, which is a continuation in part of U.S. patent application Ser. No. 12/652,845 filed Jan. 6, 2010, which is now abandoned, which is a continuation in part of U.S. patent application Ser. No. 12/210,368 filed Sep. 15, 2008, which is now abandoned, which is a continuation in part of U.S. patent application Ser. No. 11/945,674 filed Nov. 27, 2007, now U.S. Pat. No. 7,543,760, which claims the benefit of U.S. Provisional Patent Application Ser. No. 60/867,323 filed Nov. 27, 2006, the disclosures of which are incorporated herein by reference in their entirety.

FIELD OF THE INVENTION

This invention relates to a portable system for safely and efficiently producing and delivering $CO_2$ and other gases for use in medical applications.

BACKGROUND OF THE INVENTION

Conventional devices for delivering gas such as carbon dioxide ($CO_2$) for use in medical procedures typically utilize large storage tanks and regulators. Such devices are dangerous because of the risk of a seal, valve or part malfunction, which can produce a projectile in a medical setting. In addition, existing tank systems are quite expensive, extremely cumbersome and usually impractical to transport to off-site locations. These systems typically require a considerable amount of storage space. Current tanks also require filling at a filling station, which can involve the transport of a large quantity of gas such as $CO_2$. Pressurized gas tanks can explode in the event of a motor vehicle crash. Re-fillable tanks cart also exhibit rust, bacteria and contamination, which are not acceptable in a medical environment.

SUMMARY OF THE INVENTION

The present invention is intended to provide a portable, safe, reliable, and convenient source of medical gas such as $CO_2$ to health care professionals in hospital or medical office settings where a small volume of $CO_2$ or other gases is needed. The device is intended for general use by physicians and is not intended to be used for any specific medical treatment or procedure. The present invention is simple to manufacture and use because it does not require large regulators, an external power source, cumbersome large tanks or impellers for dispensing medical grade $CO_2$.

The portable apparatus of the present invention utilizes a source of compressed gas to produce the desired pressure and airflow for the effective transformation of medical $CO_2$ liquid to medical grade $CO_2$ gas.

The present invention provides for a novel portable apparatus for delivering a medical grade gas such as $CO_2$. In a preferred embodiment the apparatus includes a portable compressed gas unit having at least one cylinder containing a compressed medical gas. A solenoid valve is communicably connected to the cylinder. There is a separate pressure adjustable gas regulator for selectively adjusting the pressure of the compressed gas provided from the cylinder to the solenoid. A source of electrical power is connected to the solenoid and an electronic switch is interconnected between the source of electrical power and the solenoid. The switch is adapted to be manually activated by a selected amount of voluntary fingertip pressure for selectively opening the solenoid to transmit pressure adjusted gas therethrough. A conduit is communicably attached to an outlet of the solenoid for delivering the transmitted gas to a destination where the gas may be used in a medical procedure or stored for later use.

The compressed gas may be any gas suitable for medical applications. Suitable compressed gases may include carbon dioxide, atmospheric air, nitrogen, helium and/or mixtures thereof. The compressed gas is contained in one or more compressed gas containers such as cylindrical cartridges. The electrical power source may be delivered by batteries providing between about 3-24 volts. Preferably, the electronic switch activates the solenoid when the switch is selectively depressed by fingertip pressure.

The conduit may include a hose and the destination may include a gas storage container. The container may include a reservoir bag or other reservoir or receptacle.

The system of this invention is particularly beneficial for delivering $CO_2$ for medical use. In medical uses, $CO_2$ is used because it is safer and has fewer complications than air or oxygen in the same uses. $CO_2$ diffuses more naturally in body tissue and is absorbed in the body more rapidly with fewer side effects. $CO_2$ is used in decompartmentalization of tissues, arteries, veins and nerves and for radiological imaging, cardiac imagining, evaluation of vascularity of the heart and surrounding tissues, oncology and urology diagnostics. It is specifically used for imaging by infiltrating the tissues, body cavities and abdomen for better visualization. The $CO_2$ can also expand internal body cavities and tissues thereby enabling better diagnostic techniques.

The pressure adjusted $CO_2$, gas provided by the system of this invention is ultimately delivered to a reservoir of the physician's choice. For example, the $CO_2$ or other gas may be delivered to a medical reservoir bag or other system for temporary storage. The bag is a reservoir that is used to house the $CO_2$ provided from existing $CO_2$ tanks. The stored $CO_2$ may be used as needed by various medical devices for applications such as imaging, differentiation of tissues, arterial/venus/neurological separation, and treatment of stretch marks, facial wrinkles and dark circles. The separate pressure regulator interconnected between the gas container and the solenoid allows the pressure of the $CO_2$ or other gas to be controlled from about 0 psi to 120 psi. This allows the gas to be used for a variety of medical applications.

The system is portable, compact, and electronic so that it is convenient to utilize in the field for portable medical uses, military field uses and any other use requiring $CO_2$ or other medical gas for its performance. The system is safer than existing tank systems because it eliminates the risk of seal, valve or part malfunction, the potential for a disastrous explosion and the unwanted production of projectiles in a medical setting. It also eliminates the rust, dirt, bacteria and contaminants that can be present in refillable tanks. The system requires very little space to store and is much easier to use with a simple push button actuator to initiate operation using fingertip pressure. The system of the invention is much less expensive than current tank systems. In addition, the system utilizes compact compressed gas cartridges which can be delivered and transported in a small box. The compressed gas cartridges do not have to be transported to a filling station and do not present a risk of explosion in the event of a motor vehicle accident.

BRIEF DESCRIPTION OF THE DRAWINGS

Other objects, features and advantages will occur from the following description of a preferred embodiment and the accompanying drawings, in which.

DETAILED DESCRIPTION OF PREFERRED EMBODIMENTS

Figure 1:
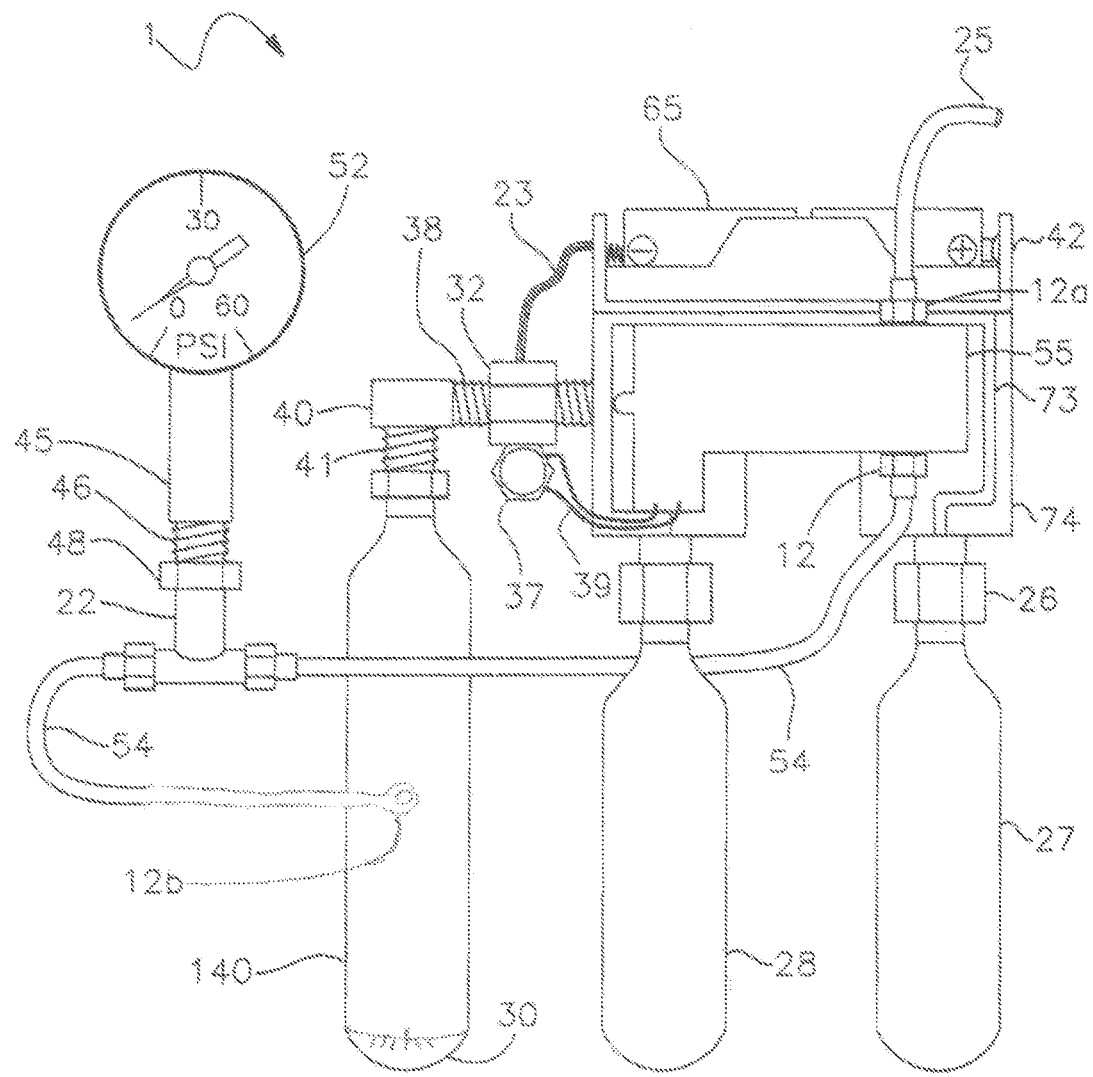
FIG. 1 is a side perspective and partly schematic view of a preferred compressed gas unit in accordance with this invention including compressed gas ($CO_2$) cylinders, a pressure adjustable regulator and a separate solenoid.

In FIG. 1, compressed gas unit 1 comprises a solenoid 55 with at least one compressed gas ($CO_2$; cylinder 27 connected communicably to the solenoid. In one embodiment, compressed gas cylinder or cartridge 27 is 25 g or larger. Compressed gas cylinder 27 is secured into position to unit 1 by means of cylinder cartridge puncture valve 26 and a fitting 74. In a preferred embodiment, cylinder cartridge puncture valve 26 has a mechanism for piercing cylinder 27, as is known in the art, and for holding or securing said cylinder in place. Compressed air is delivered to solenoid 55 from compressed gas cylinder 27 through cylinder cartridge puncture valve 26 and channel 73 of fitting 74. Conduit 73 of fitting 74 communicates with a threaded conduit 38 described more fully below.

Compressed gas unit 1 has at least one battery 65 held in place by battery holder 42, for providing electrical power by which solenoid 55 may be selectively activated and opened by a pressure activation switch or actuator 37. The switch is designed so that solenoid 55 is opened when a physician or other medical personnel engages the switch by voluntarily applying a small predetermined amount of fingertip pressure to switch 37. It is not activated by a breathing sensor or other actuators designed to be operated by involuntary movement of the user's body. Battery 65 supplies power to solenoid 55 through switch wire assembly 23, which is connected to activation switch 37. This switch is mounted to a pressure nut 32 carried on threaded conduit 38. Compressed air unit 1 has electrical wiring 39 for providing necessary electricity from switch 37 to solenoid 55

Unit 1 also comprises a separate black rock regulator 140, which is distinct from solenoid 55. Regulator 140 is controlled or adjusted by a regulator adjustment knob 30 to provide a selected level of pressure to the gas provided to the solenoid. Black rock regulator 140 is communicably connected to unit 1 by an elbow pipe 40. The elbow pipe includes a threaded vertical conduit segment 41 joined to regulator 140 through a connector nut and the threaded horizontal conduit 38, which is engaged by pressure nut 32.

Compressed gas cylinder 27 is secured to unit 1 by cartridge puncture valve 26 as is commonly known. In one embodiment, compressed gas cylinder 27 is a 25 g cylinder. Alternative capacities (e.g. 16, 33, 45 grams) may be used within the scope of this invention. Compressed air leaves black rock regulator 140 at the regulator adjusted pressure through a 10/32" hose port 12b and flows through a hose junction 22, by means of ⅛" pressure hose 54, until reaching the 10/32" hose port 12 affixed to solenoid 55. From hose port 12, the compressed air enters solenoid 55 Compressed air unit 1 also has an outlet air port 25, which is connected to solenoid 55 through intermediate 10/32" hose port 12a for transporting compressed gas, namely $CO_2$, from solenoid 55 in compressed gas unit 1 to the storage container or other destination for medical gas whenever the solenoid is opened. Outlet gas may be monitored with pressure gauge 52 connected to hose junction 22 through a conduit 45 having threads 46. The threaded end of conduit 45 interengages a nut 48 carried by hose junction 22.

In certain embodiments a second compressed gas cylinder or cartridge 28, featuring a 16 g or 25 g compressed gas cylinder, may be used in addition to or in lieu of gas cylinder 27. In still other embodiments a larger compressed gas cylinder and expansion chamber may be substituted for the gas cartridges previously described in accordance with the invention. The size and number of compressed gas containers are not limitations of the invention.

Figure 2:
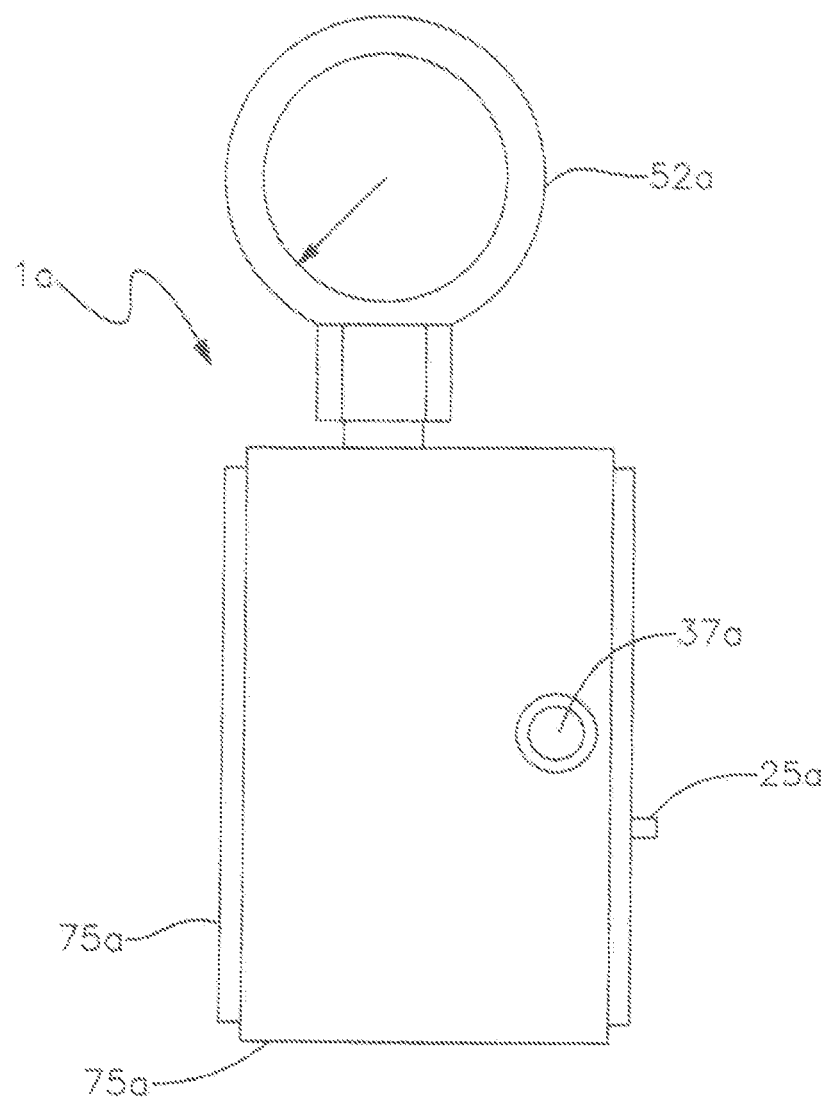
FIG. 2 is a schematic front view of an alternative compressed gas unit enclosed in a housing.
Figure 3:
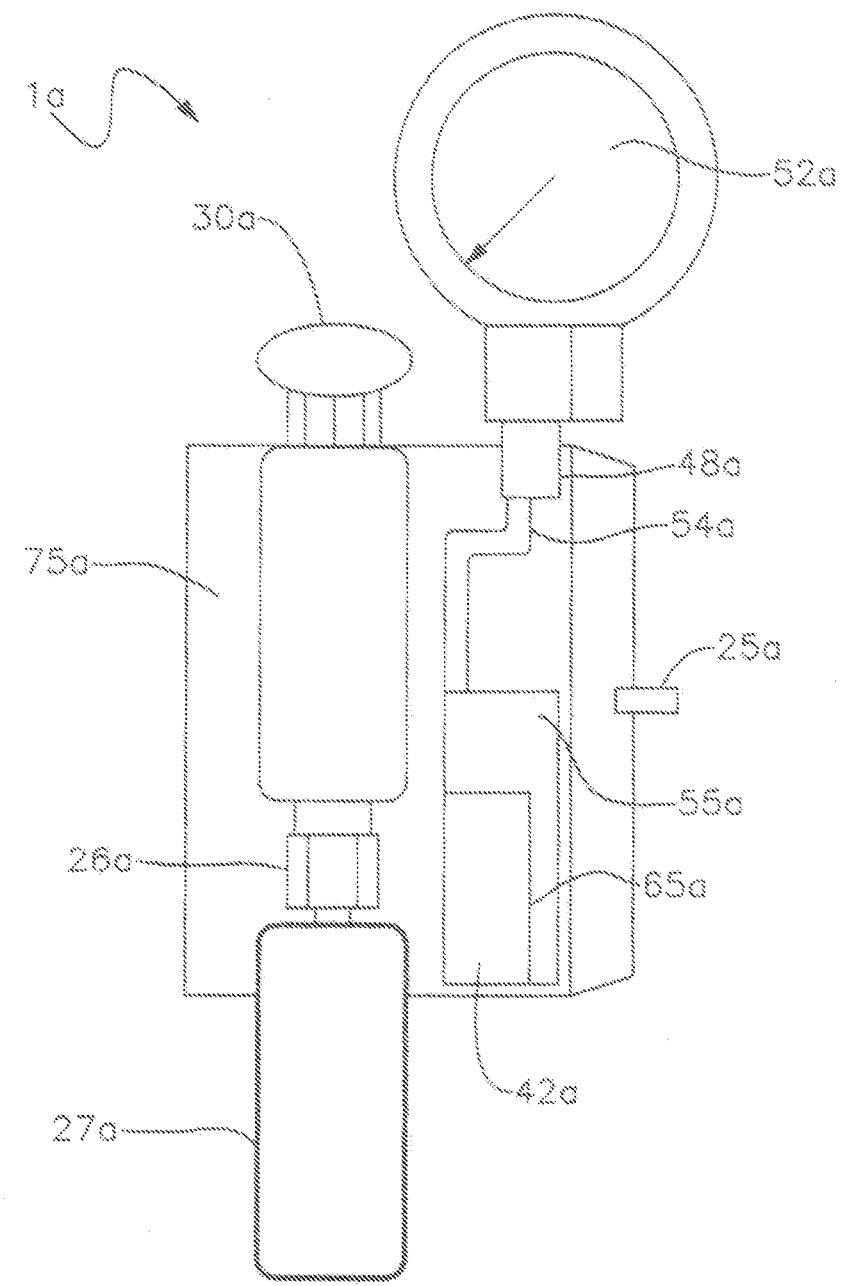
FIG. 3 depicts a schematic layout of the components of the compressed gas unit of FIG. 2.

FIGS. 2 and 3 depict an alternative embodiment of a compressed gas unit 1a wherein various components of the gas unit are enclosed in a housing 75a. The components of unit 1a are designated by reference numerals that correspond to those of the previously described embodiment and further include lower case "a" designations. In particular, a $CO_2$ cartridge 27a is connected by a puncture valve 26a to a regulator 140a. The regulator is controlled by an adjustment knob 30a. Regulator 140a is connected through a conduit 54a to both a pressure gauge 52a and a solenoid 55a. More particularly, gauge 52a is connected to a coupling 48a. Solenoid 55a is powered by a battery 65a, which is itself held in place within the housing by a holder 42a. A user accessible Luer fitting 25a is communicably connected to solenoid 55a and extends exteriorly of housing 75a.

Unit 1a is activated to selectively open solenoid 55a by manually engaging switch 37a through voluntary fingertip pressure. This transmits the pressure regulated $CO_2$ or other gas through solenoid 55a and fitting 25a. The compressed gas unit thereby operates in a manner analogous to that previously described to provide pressure adjusted $CO_2$ from cartridge 27a through Luer fitting 25a to a gas storage container or other destination for the medical gas. The following are preferred examples of such applications.

Examples of Use

It is contemplated that the apparatus of the present invention be used in methods and procedures requiring delivery of medical gas. The following are examples of such applications:

$CO_2$ is useful in the following arterial procedures: abdominal aortography (aneurysm, stenosis) iliac arteriography (stenosis), runoff analysis of the lower extremities (stenosis, occlusion), renal arteriography (stenosis, arteriovenous fistula [AVF], aneurysm, tumor), renal arterial transplantation (stenosis, bleeding. AVF), and visceral arteriography (anatomy, bleeding, AVF, tumor).

$CO_2$ is useful in the following venous procedures: venography of the upper extremities (stenosis, thrombosis), inferior vena cavography (prior to fitter insertion), wedged hepatic venography (visualization of portal vein), direct portography (anatomy, varices), and splenoportograpy (visualization of portal vein).

$CO_2$ is likewise useful in the following interventional procedures: balloon angioplasty (arterial, venous), stent placement (arterial, venous), embolization (renal, hepatic, pelvic, mesenteric) transjugular intrahepatic portacaval shunt creation, and transcatheter biopsy (hepatic, renal).

Angiography is performed by injecting microbubbles of $CO_2$ through a catheter placed in the hepatic artery following conventional hepatic angiography. Vascular findings on US angiography can be classified into four patterns depending on the tumor vascularity relative to the surrounding liver parenchyma, hypervascular, isovascular, hypovascular, and a vascular spot in a hypovascular background.

Improved CT colonography, an accurate screening tool for colorectal cancer, is performed using a small flexible rectal catheter with automated $CO_2$ delivery. This accomplishes improved distention with less post-procedural discomfort.

Carbon dioxide ($CO_2$) gas is used as an alternative contrast to iodinated contrast material. The gas produces negative contrast because of its low atomic number and its low density compared with the surrounding tissues. When injected into a blood vessel, carbon dioxide bubbles displace blood, allowing vascular imaging. Because of the low density of the gas, a digital substraction angiographic technique is necessary for optimal imaging. The gas bubble can be visible on a standard radiograph and fluoroscopic image.

$CO_2$ insufflation for colonoscopy improves productivity of the endoscopy unit.

Endoscopic thyroid resection involves creating a working space within the neck using $CO_2$ insufflation devices, with both axillary and neck approaches as starting points for dissection.

$CO_2$ unsuffiators are used during laparoscopic surgery.

Because of the lack of nephrotoxicity and allergic reactions, $CO_2$ is increasingly used as a contrast agent for diagnostic angiography and vascular interventions in both the arterial and venous circulation.

$CO_2$ is particularly useful in patients with renal insufficiency or a history of hypersensitivity to iodinated contrast medium.

$CO_2$ is compressible during injection and extends in the vessel as it exits the catheter.

$CO_2$ is lighter than blood plasma; therefore, it floats above the blood. When injected into a large vessel such as the aorta or inferior vena cava, $CO_2$ bubbles flow along the anterior part of the vessel with incomplete blood displacement along the posterior portion.

CO2 causes no allergic reaction. Because $CO_2$ is a natural byproduct, it has no likelihood of causing a hypersensitivity reaction. Therefore, the gas is an ideal alternative. Unlimited amounts of $CO_2$ can be used for vascular imaging because the gas is effectively eliminated by means of respiration.

$CO_2$ is partially useful in patients with compromised cardiac and renal function who are undergoing complex vascular interventions.

Intranasal carbon dioxide is very promising as a safe and effective treatment to provide rapid relief for seasonal allergic rhinitis.

$CO_2$ is used for transient respiratory stimulation; encouragement of deep breathing and coughing to prevent or treat aterectasis; to provide a close-to-physiological atmosphere (mixed with oxygen) for the operation of artificial organs such as the membrane dialyzer (kidney) and the pump oxygenator; and for injection into body cavities during surgical procedures.

Medical asepsis is accomplished by using $CO_2$ on implant devices prior to surgical implantation. $CO_2$ may be effectively delivered to a foam generating tip for creating a medical foam for use in wound care and hair loss treatment.

Additionally, the present invention is used in methods requiring the deliver of other gasses such as: Carbon Dioxide U.S.P.; Medical Air U.S.P., Helium U.S.P., Nitrogen U.S.P., Nitrous Oxide U.S.P., Oxygen U.S.P. and any combination thereof.

In one embodiment, the present invention provides for an apparatus and use in a method whereby delivery of a gas alone is desired. The delivery of gas is independent of systems whereby a gas is delivered as a carrier for medications or other materials.

While the invention has been described in its preferred form or embodiment with some degree of particularity, it is understood that this description has been given only by way of example, and that numerous changes in the details of construction, fabrication, and use, including the combination and arrangement of parts, may be made without departing from the spirit and scope of the invention.

Although specific features of the invention are shown in some of the drawings and not others, this is for convenience only, as each feature may be combined with any and all of the other features in accordance with this invention.

Other embodiments will occur to those skilled in the art and are within the following claims:

1. An apparatus for dispensing medical grade gas, said apparatus comprising:
    a portable compressed gas unit including:
        a housing including a cylinder cartridge puncture valve adapted for attachment to a source of compressed gas,
        a solenoid communicably connected to the source of compressed gas, the solenoid including an inlet and an outlet,
        a pressure adjustable gas regulator separate and distinct from the solenoid, the gas regulator being connected to the source of compressed gas via a pipe and being connected to the solenoid by a hose such that the gas regulator is communicably interconnected between the source of compressed gas and the inlet of the solenoid for selectively adjusting the pressure of the gas provided from the source of compressed gas to the solenoid, the gas regulator including a regulator adjustment knob to provide a selected level of pressure,
        a pressure gauge connected to a junction secured along the hose connecting the gas regulator to the solenoid such that the pressure gauge is between the gas regulator and the solenoid to provide information regarding the pressure being supplied to the solenoid, and
        a pressure activated electric switch engaged to selectively open the solenoid; and
    a conduit communicably attached to the outlet of the solenoid for transmitting gas to a destination for storage or use in a medical application when the solenoid is opened by operation of the pressure activated electric switch.

2. The apparatus of claim 1 wherein the compressed gas includes at least one of carbon dioxide, atmospheric air, helium and oxygen.

3. The apparatus of claim 1 wherein the compressed gas is contained within a replaceable compressed gas cartridge.

4. The apparatus of claim 1 in which the pressure activated electric switch includes an electronic push button device.

* * * * *